United States Patent [19]

Clayton

[11] Patent Number: 4,772,733
[45] Date of Patent: Sep. 20, 1988

[54] EPOXY-AZIDES

[75] Inventor: Anthony B. Clayton, Wilmington, Del.

[73] Assignee: Hercules Incorporated, Wilmington, Del.

[21] Appl. No.: 99,868

[22] Filed: Sep. 22, 1987

Related U.S. Application Data

[63] Continuation-in-part of Ser. No. 886,477, Jul. 17, 1986, abandoned.

[51] Int. Cl.⁴ .............................................. C07D 303/22
[52] U.S. Cl. .................................... 549/551; 549/525; 260/349
[58] Field of Search ........................................ 549/551

[56] References Cited

U.S. PATENT DOCUMENTS 4,240,971 12/1980 Breslow .......................... 260/348.43
4,352,938 10/1982 Breslow .............................. 549/553

Primary Examiner—Norma S. Milestone
Attorney, Agent, or Firm—Marion C. Staves

[57] ABSTRACT

An epoxy-sulfonylazide having the general formula

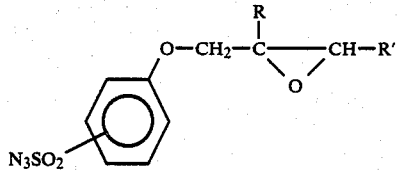

wherein R is lower alkyl and R' is hydrogen or lower alkyl.

3 Claims, No Drawings

EPOXY-AZIDES

This application is a continuation-in-part of U.S. application Ser. No. 886,477, which was filed July 17, 1986, abandoned.

The invention relates to epoxy compounds and, in particular, to epoxy-sulfonylazides.

Epoxy-sulfonylazide compounds are known as bonding agents for polymers and other materials, such as disclosed in U.S. Pat. No. 4,240,971. However, these known bonding agents are relatively time consuming to produce.

Accordingly, it is an objective of the instant invention to produce a novel epoxy-sulfonylazide that is useful as a bonding agent for polymers and other materials, and which can be made in a relatively short time. Other objectives of the instant invention will be apparent from the disclosure herein.

According to the instant invention, an epoxy-sulfonylazide is characterized in that it has the general formula

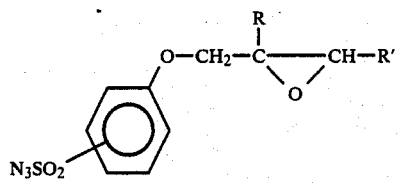

wherein R is lower alkyl and R' is hydrogen or lower alkyl. Lower alkyl as used herein means a $C_1$–$C_4$ alkyl.

Exemplary epoxy-sulfonylazides of the instant invention are 3-(para-azidosulfonylphenoxy)-2-methylpropylene oxide. 3-(para-azidosulfonylphenoxy)-2-ethylpropylene oxide, 3-(ortho-azidosulfonylphenoxy)-2-methylpropylene oxide, 3-(meta-azidosulfonylphenoxy)-2-methylpropylene oxide, and 3(para-azidosulfonylphenoxy)-2-methylbutene oxide. Preferred is 3-(para-azidosulfonyl-phenoxy)-2-methylpropylene oxide.

Preferably, the epoxy-sulfonylazide of the instant invention is made by epoxidation of an unsaturated sulfonylazide with a per-acid, e.g., perbenzoic acid, m-chloroperbenzoic acid, or peracetic acid. Peracetic acid is preferred. The temperature for the epoxidation varies from about 20° C. to about 60° C., depending on the amount and type of epoxidation agent used. The time required depends on the amount and type of epoxidation agent and the temperature used. Generally, the time varies from about one hour to about seventy-two hours. Generally, an excess amount of epoxidation agent is used, based on the number of moles of unsaturated sulfonylazide used, preferably in the range of about 1.1 to about 3 times the number of moles. The epoxidation is carried out in any inert organic solvent in which the unsaturated sulfonylazide is soluble such as, for example, acetic acid, methylene chloride, ethylene chloride, toluene, xylene, ethyl acetate, hexane, heptane, and other aromatic, ester, and hydrocarbon solvents. The above unsaturated sulfonylazide is preferably prepared by alkylation of a phenolic sulfonic acid salt, followed by sulfochlorination with phosphorous pentachloride or thionyl chloride and reaction of the resulting unsaturated sulfonyl chloride with sodium azide. The details for the above preparation are given in Example 1.

The epoxy-sulfonylazide of the instant invention is useful for bonding polymers to certain other materials. This requires the useful polymers to react with the sulfonylazide group of the epoxy-sulfonylazide to bond the residue of the epoxy-sulfonylazide to the polymer. The other material to be bonded to the polymer must react with the epoxy group of the epoxy-sulfonylazide (or residue) to bond the residue (or polymer-bound residue) to the material.

Many polymers are sulfonylazide-reactive. Preferred sulfonylazide reactive polymers are hydrocarbon polymers including saturated and unsaturated, linear and non-linear, crystalline and amorphous, homopolymers, copolymers, terpolymers, and the like; for example, polyethylene, polypropylene, polystyrene, styrene butadiene rubber, butyl rubber, natural rubber, polybutadiene, polyisobutylene, ethylene-propylene copolymer, cis-1,4-polyisoprene, ethylene-propylene-dicyclopentadiene terpolymer; and blends of these polymers with each other and blends of these polymers with organic non-hydrocarbon polymers. Other examples of sulfonylazide-reactive polymers are organic non-hydrocarbon polymers including homopolymers, copolymers, and terpolymers. Typical of these organic non-hydrocarbon polymers are cellulose esters, such as, for example, cellulose acetate-butyrate, cellulose acetate-propionate, cellulose acetate, cellulose propionate, cellulose butyrate, and the like; cellulose ethers, such as, for example, hydroxyethyl cellulose, hydroxypropyl cellulose, and the like; polyesters such as poly(ethylene glycol terephthalate), drying and non-drying alkyd resins and the like; poly(alkylene oxide) polymers, such as poly(ethylene oxide), poly(propylene oxide), poly-(ethylene oxide-propylene oxide); polyamides such as nylon, and the like; allyl pentaerythritol derivatives such as, for example, the condensate of triallyl pentaerythritol with diallylidene pentaerythritol, esters of trially pentaerythritol and drying oil fatty acids, and the like; poly(vinyl alkyl ethers) such as, for example, poly(-vinyl methyl ether) and the like; poly(vinyl acetels) such as, for example, poly(vinyl butyral) and the like; vinyl chloride polymers having a vinyl chloride content of at least 10 mole percent, such as, for example, poly(-vinyl chloride), vinyl chloride-vinyl acetate copolymers, vinyl chloridevinylidene chloride copolymers, vinyl chloride-fumaric acid copolymers, vinyl chloride-vinyl acetal copolymers, such as, for example, the vinyl chloride-vinyl butyral copolymers, vinyl chloride-vinylidene chloride-acrylonitrile terpolymers and the like; nitrocellulose, chlorinated natural rubber; sulfo-chlorinated polyethylene; polysulfide rubber; polyurethane rubber; poly(vinyl acetate); ethylene-vinyl acetate copolymers; poly-acetate copolymers; poly(vinylidene chloride); vinylidene chloride-acrylonitrile copolymers; ethyl acrylate-2-chloroethyl vinyl ether copolymers; poly (ethyl acrylate); poly(ethyl methacrylate); poly[3,3-bis (chloromethyl)oxetane]; vinyl modified poly(dimethylsiloxane); polychloroprene; butadiene-acrylonitrile copolymers; and the like.

Examples of epoxy-reactive materials that are useful according to this invention include siliceous materials such as glass, asbestos, sand, clay, concrete, stone, brick, ceramic materials, etc.; metals such as aluminum, cadmium, chromium, copper, magnesium, nickel, silver, tin, iron, titanium, zinc, etc., alloys of the metals such as steel, brass, bronze, nickel chrome, etc., and including metals that have been surface treated with phosphates, chromates, etc., or metals on the surface of which oxides have formed; and epoxy-reactive polymers, e.g., hydroxy-containing polymers such as hydroxypropyl cellulose. These epoxy-reactive materials can be in various forms, such as, sheets, plates, blocks, wires, cloth, flakes, fibers and particles, etc. Basic dyes, such as basic fuchsin, are also useful examples of epoxy-reactive materials.

Various methods can be used to bond polymers to materials according to this invention.

When dying polymers according to the invention, the preferable method is to heat the sulfonylazide-reactive polymer and the epoxy-sulfonylazide. The thus treated polymer is then heated in water with the basic dye. The amount of polymer, dye, and epoxy-sulfonylazide used will vary. Generally, by polymer weight, about 2-20% dye is used and about 0.1-3% epoxy-sulfonylazide is used. The temperature to which the polymer and epoxy-sulfonylazide is heated will vary, but it must be sufficient to react the polymer with the sulfonylazide group. Generally, this will be about 120° C.-160° C. depending on the polymer and epoxy-sulfonylazide, with time varying from about 2 hours-100 hours, depending on temperature. When heating the epoxy-sulfonylazide treated polymer with the dye, the temperature must be sufficient to react the dye with the epoxy group, about 50°-100° C., depending on the material and epoxy-sulfonylazide used, with time, depending on temperature, of about 0.5-4 hours.

When bonding polymers to siliceous flake materials according to this invention, it is preferable to first dry-blend the epoxy-sulfonylazide with the epoxy-reactive material and the sulfonylazide-reactive polymer. The dry blend is then heated to a temperature sufficient to react the polymer with the sulfonylazide group of the epoxy-sulfonylazide and the particulate material with the epoxy group. The temperature varies from about 120°-250° C., depending on the epoxy-sulfonylazide, polymer, and material used, and the time is dependent on the temperature, from about 1 second -24 hours. Amounts of particulate material, polymer, and epoxy-sulfonylazide will vary—epoxy-sulfonylazide at about 0.1-3% of siliceous flake material weight and siliceous flake material at about 10-50% of polymer weight.

Another use of the instant invention is bonding a polymer to a rigid substrate. The preferred method is to first heat the sulfonylazide-reactive polymer and epoxysulfonylazide to a temperature sufficient to react the polymer and the sulfonylazide group of the epoxy-sulfonylazide; this is in the range of about 120°-160° C., based on the polymer and epoxy-sulfonylazide used, and for a time of about 0.5-4 hours, based on the temperature used. Then, the thus reacted polymer is contacted with the substrate and heated to a temperature sufficient to bond the epoxy group of epoxy-sulfonylazide residue with the substrate, typically about 190°-250° C., for a time, dependent on temperature, of about 5 seconds to 10 minutes.

The following Examples are included to more clearly illustrate the instant invention, however, the invention is not intended to be limited thereby. All parts and percentages in the Examples are by weight unless indicated otherwise.

EXAMPLE 1

A. Preparation of Unsaturated Sulfonyl Azide

3-Chloro-2-methylpropene (methallyl chloride) (91 g, 1.0 mole) is added dropwise to a stirred and refluxing mixture of p-phenolsulfonic acid sodium salt dihydrate (232 g, 1.0 mole) and sodium hydroxide (41 g, 1.025 mole) in water (500 cc) and acetone (500 cc). After the addition the mixture is stirred and refluxed for 20 hours. The solution is cooled to 17° C. and the white precipitate which formed is collected. The filtrate is washed twice with ether and cooled to 10° C. and a further precipitate is collected. The filtrate is reduced in volume, cooled to 15° C. and a further precipitate is collected. The solids are combined and dried by azetroping with ethylene dichloride until no more water is collected. The total combined weight of the p-methallyloxybenzenesulfonic acid sodium salt is 203 g (81 percent yield).

Thionyl chloride which is distilled from triphenyl phosphite (114 g, 0.95 mole) is added to a stirred mixture of p-methallyloxybenzenesulfonic acid sodium salt (203 g, 0.81 mole) and ethylene dichloride (500 cc). Dimethylformamide (13.9 cc) is added in three portions. The mixture is stirred and refluxed for 3.5 hours. The mixture is then cooled to room temperature and poured into a solution of sodium bicarbonate (15 g) in water (682 cc). The pH of the water layer is 7.5. The mixture is filtered and the lower organic layer is separated and washed three times with water and dried over magnesium sulfate. A portion of the solution is evaporated to dryness under reduced pressure to give the sulfonyl chloride as a yellow liquid. In total, 207 g of p-methallyloxybenzenesulfonyl chloride is obtained. The Infrared and NMR spectra are consistent with the desired structure.

A solution of sodium azide (80 g, 1.23 mole) in water (300 cc) is added dropwise to a stirred mixture of p-methallyloxybenzenesulfonyl chloride (207 g, 0.84 mole), ethylene dichloride (600 g and Aliquat ® 336 (2.0 g) (phase transfer agent). The temperature rises to 32° C. during the addition. The mixture is stirred for a further two hours at room temperature. The organic layer is separated from the water layer and washed with 5 weight percent sodium bicarbonate (250 cc), water (300 cc two times) and dried over magnesium sulfate. The yield of p-methallyloxybenzenesulfonyl azide is 208 g.

B. Preparation of Epoxy-Sulfonylazide

To exemplify making an epoxy-sulfonylazide of the instant invention, 255 parts of 35 peracetic acid in acetic acid are added dropwise to a stirred solution of paramethallyloxybenzenesulfonylazide (208 parts) in ethylene dichloride (600 parts) to which has been added sodium acetate (10 parts) to neutralize the sulfuric acid present in the peracetic acid keeping the temperature below 30° C. After the addition, the mixture is stirred at room temperature for 68 hrs, 10% sodium sulfite solution is added in portions, testing with starch-iodide paper until a negative test is obtained. The organic layer is separated and washed with 10% sodium bicarbonate until the washes remain alkaline, dried over magnesium sulfate, and the methylene chloride is evaporated off under reduced pressure to leave the epoxy-sulfonylazide as a pale yellow liquid, which crystallizes on standing. Obtained are 191.56 parts of epoxy-sulfonylazide, which is 87% of theoretical. The product is over 95% pure by NMR analysis. After recrystallization from ethanol the pure compound is a white, crystalline solid having a melting point of 60° C.

EXAMPLE 2

To show another example of the epoxy-sulfonylazide of the instant invention, a solution of p-methallyloxybenzenesulfonylazide (506 parts) in methylene chloride (1,450) parts is stirred and heated to reflux (41° C.) then a solution of 35% peracetic acid in acetic acid (521.5 parts) containing sodium acetate (15.6 parts) is added slowly from an addition funnel over 15 minutes. An additional 40 parts of methylene chloride is added to adjust the reflux temperature to 45° C. After 6 hrs stirring and refluxing at 45° C. the reaction is quenched with 835 parts of distilled water. The layers are separated and the organic phase is washed with 555 parts of 10% sodium sulfite, 835 parts of sodium bicarbonate, and 565 parts of distilled water containing 23 parts of trioctylammonium chloride. The solution is dried azeotropically, and the solvent is removed at 55° C. and 20 mm to yield 528 parts of 3-(p-azidosulfonylphenoxy)-2-methylpropylene oxide as a white, crystalline solid. This represents a yield of 98%.

EXAMPLE 3

To exemplify the epoxy-sulfonylazide of the instant invention as a dyesite for basic dyes, 3-(para-azidosulfonylphenoxy)-2-methylpropylene oxide is slurried into a methylene chloride solution of polypropylene flake (melt flow 4 dg/min according to ASTM D1238-65T @230° C., intrinsic viscosity in decahydronaphthalene @135° C. is 2.5–3.0 dl/g) at a level of 0.5% by weight of polypropylene, and then the solvent is evaporated off on a rotary evaporation under vacuum. The polymer is stabilized with 0.25 phr (i.e., parts per hundred polymer) distearylthiodipropionate, 0.12 phr phenolic stabilizer (50/50 blend of tetrakis[methylene[3,5-ditertbutyl-4-hydroxyhydrocinnamate]]and tris[2,4-ditertbutylphenolphosphite]) and 0.1 phr calcium stearate, then heated under nitrogen at 155° C. for 3 hours.

Fifty parts of the stabilized polymer is added to 3.3 parts Basic Fuchsin dye, 1 part formic acid, and 1 part surfactant (nonylphenol ethylene oxide adduct) in 1570 parts water (pH=3). This is stirred and boiled for 1 hour and 15 minutes. It is then filtered, rinsed with water to remove unreacted dye, and dried. The resulting dyed flake is compression-molded into plaques at 400 to 1600 lb/sq.in. for 2 minutes. The plaques are evenly dyed.

EXAMPLE 4

To exemplify the epoxy-sulfonylazide as a bonding agent, mica flake is treated with 3-(para-azidoslfonylphenoxy)-2-methylpropylene oxide at a level of 0.5%, by weight of mica, by slurrying a solution of the azide in methylene chloride onto the mica, and allowing the solvent to evaporate. Six parts of polypropylene is stabilized as in Example 3 and blended with 4 parts of the treated mica. The stabilized polypropylene is also blended with an untreated mica control at a 6:4 ratio, and test specimens are compression-molded from the blends. Flexural properties (Strength and Modulus) and heat deflection temperature are determined of the specimens using ASTM D790 and D648, respectively. The results obtained are recorded in Table 1.

TABLE 1

| Sample | Flexural Strength* (psi) | 1% Secant Flexural Modulus* (psi) | Heat Deflection Temp. @264 psi(°C.) 2 Test Runs |
|---|---|---|---|
| Untreated Control | 5,542 | 510,632 | (114)(114) |
| 0.5% Epoxy-sulfonylazide | 6,572 | 644,538 | (126)(127) |

*average of 5 determinations

EXAMPLE 5

To illustrate the epoxy-sulfonylazide of the instant invention as a bonding agent for polymers and aluminum, stabilized ethylene/propylene copolymer flake (7% ethylene, melt flow 4 dg/min according to ASTM D1238-65T @230° C., intrinsic viscosity is 2.5–3.0 dl/g in decahydronaphthalene @135° C.) is treated as in Example 1 with 3-(para-azidosulfonylphenoxy)—2-methylpropylene oxide using various amounts by weight percent of the copolymer as listed in Table 2 below, and stabilized with a phenolic stabilizer (as used in Example 3) at 0.12 phr. Samples of the treated polymer are placed between test panels of chromium oxide-treated aluminum, and pressed at 800 lb./sq.in. for 1.5 minutes at 200° C. Test specimens are cut, and 90° C. T-peel determinations are made using ASTM D1876. The results obtained are the average of five determinations and are given in Table 2.

TABLE 2

| Treatment Level Epoxy-Sulfonylazide (%) weight of copolymer | 90° T-peel (lb/in) |
|---|---|
| 0 | 1.5 |
| 0.25 | 84 |
| 0.5 | 69.3 |
| 1 | 106.3 |
| 2 | 96.5 |

What is claimed is:

1. An epoxy-sulfonylazide having general formula

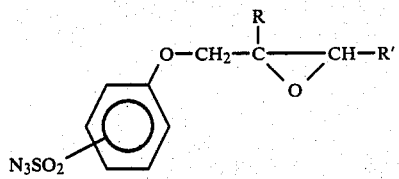

wherein R is lower alkyl and R' hydrogen or lower alkyl.

2. The epoxy-sulfonylazide according to claim 1, wherein R is methyl.

3. 3-(para-azidosulfonylphenoxy)-2-methylpropylene oxide.

* * * * *

UNITED STATES PATENT AND TRADEMARK OFFICE
CERTIFICATE OF CORRECTION

PATENT NO. : 4,772,733

DATED : SEPTEMBER 20, 1988

INVENTOR(S) : Anthony B. Clayton

It is certified that error appears in the above-identified patent and that said Letters Patent is hereby corrected as shown below:

Column 2, line 39;

"acetels" should read --acetals-- .

Column 4, line 48;

"35" should read --35%-- .

Column 3, line 9;

"dying" should read --dyeing--.

Signed and Sealed this

Twenty-eighth Day of February, 1989

Attest:

DONALD J. QUIGG

*Attesting Officer*     *Commissioner of Patents and Trademarks*